United States Patent [19]

Ohkuma et al.

[11] Patent Number: 5,208,364

[45] Date of Patent: May 4, 1993

[54] ANTIBIOTIC 5-LIPOXYGENASE INHIBITORS

[75] Inventors: Hiroaki Ohkuma; Yutaka Hoshino; Yosuke Sawada, all of Tokyo, Japan; Derek Hook, Roxbury, Conn.

[73] Assignee: Bristol-Myers Squibb Co., New York, N.Y.

[21] Appl. No.: 904,412

[22] Filed: Jun. 25, 1992

[51] Int. Cl.$^5$ .......................................... C07C 229/00
[52] U.S. Cl. ...................................... 560/46; 435/183; 435/253.5; 435/41
[58] Field of Search ........................... 560/46; 514/534

[56] References Cited

U.S. PATENT DOCUMENTS 4,861,798  8/1989  Tramposch et al. ................. 514/575

FOREIGN PATENT DOCUMENTS 3303959  12/1988  Japan .

OTHER PUBLICATIONS

Elsevier et al, "Haemodynamics, Hormones and Inflammations", *Discoveries in Pharmacology*, vol. 2, (1984), pp. 523–553.

Taylor et al, *Trends Pharmacal. Sci*, vol. 7, (1986), p. 100.

Sirois, *Adv. Lipid Res.* vol. 21, (1985), p. 79.

Dahlen et al, "*Nature*", vol. 288, (1980), p. 484.

Ford-Hutchinson, "*J. R. Soc. Med,*" vol. 74, (1981), p. 831.

Camp et al, "*Prostaglandins*", vol. 26, (1983), p. 432.

Cashman, J. R. "*Pharm. Res.*", (1985), p. 253.

Kitamura et al, "Novel Microbial Products for Medicine and Agriculture", *Society for Industrial Microbiology*, Chapter 17, (1989), pp. 145–150.

Tramposch et al, "Biochemical and pharmacological properties of a new topical antiinflammatory compound, 9-phenylnonano-hydroxamic acid", *Agents and Actions*, vol. 30, (1990), p. 443.

*Primary Examiner*—Paul J. Killos
*Attorney, Agent, or Firm*—Sandra M. Nolan

[57] ABSTRACT

Novel compounds derived from cultures of Streptomyces sp. AA2807 are useful as 5-lipoxygenase inhibitors.

6 Claims, 5 Drawing Sheets

ANTIBIOTIC 5-LIPOXYGENASE INHIBITORS

BACKGROUND

Enzymes that catalyze the oxidative metabolism of arachidonic acid have provided fertile ground for the development of useful therapeutic agents. Inhibitors of the enzyme cycloxygenase prevent the formation of the prostaglandins and thromboxanes and are clinically useful anti-inflammatories and peripheral analgesics. See *Discoveries in Pharmacology*, 2, "Haemodynamics, Hormones and Inflammations", Parnham and Bruinvels, eds., Elsevier: Amsterdam, (1984), pp. 523-553.

Recently, it has been discovered that the enzyme 5-lipoxygenase (5-LPO) catalyzes the first step in the formation of a series of biologically important metabolites of arachidonic acid, the leukotrienes (LT). See Taylor, G. N. and Clarke, S. R.: *Trends Pharmacal. Sci* (1986) 7, 100 and Sirois, P.: *Adv. Lipid Res.* (1985), 21, 79. In particular, leukotrienes $LTC_4$ and $LTD_4$ have been identified as the slow-reacting substance of anaphylaxis (SRSA) and cause a prolonged contraction of bronchial smooth muscle. This was reported by Dahlen, S., Hedqvist, P., Hammarstrom, S. and Samuelsson, B. In *Nature* (1980),288, 484. $LTB_4$ has been shown by A. W. Ford-Hutchinson to be a powerful chemotactic agent for a variety of cell types. Ford-Hutchinson, A. W.: *J. R. Soc. Med* (1981) 74 831. This evidence suggests that an inhibitor of 5-LPO may be useful in the treatment of asthma, immediate hypersensitivity, and inflammation.

The leukotrienes are believed to play a symptomatic or causative role in the dermatological condition psoriasis. Psoriasis is a chronic proliferative disease of the skin whose lesions are characterized by the accumulation of polymorphonuclear leukocytes (PMNs). $LTB_4$, along with other metabolites of arachidonic acid, has been found at elevated concentrations in the involved skin of psoriatic patients. Camp, R. D. R., Mallet, A. I., Woolard, P. M., Brain, S. D., Kobza-Black, A. and Greaves, M. W.: *Prostaglandins* (1983), 26, 432. It is therefore reasonable that a potent topical inhibitor of leukotriene biosynthesis would be therapeutically useful in the treatment of psoriasis.

Various strategies have been employed in attempts to develop useful inhibitors of 5-LPO. Two articles dealing with such attempts are: Cashman, J. R.: *Pharm. Res.* (1985), 253; and Kitamura, S., Hashizume, K., Iida, T., Ohmori, K. and Kase, H.: "Novel Microbial Products for Medicine and Agriculture", Demain, Somkuti, Hunter-Cevera and Rossmore, eds., Society for Industrial. Microbiology (1989), Chapter 17, pp. 145-150.

Tramposch et. al., in U.S. Pat. No. 4,861,798, discuss novel 5-LPO inhibitors.

Also, 9-phenyl-agnano-hydroxamic acid is described by Tramposch, K. M., Zusi, F. C., Marathe, S. A., Stanley, P. L., Nair, X., Steiner, S. A., and Quigley, J. W. in "Biochemical and pharmacological properties of a new topical anti-inflammatory compound, 9-phenylnonanohydroxamic acid", *Agents and Actions* (1990), 30, 443.

THE INVENTION

Applicants have discovered novel antibiotic 5-LPO inhibitory compounds which were derived via the fermentation of certain microorganisms.

In preferred embodiments, the isodecyl, isoundecyl and isolauryl esters of 5-hydroxyanthranilic acid are isolated from fermentates of Streptomyces sp. AA2807 via suitable solvent extraction, column chromatography and preparative high pressure liquid chromatography (HPLC).

Applicants' references to "the compound(s)" are intended to include all pharmaceutically acceptable derivatives of same.

Streptomyces sp. AA2807, isolated from a soil sample collected in Nagatoro, Saitama prefecture, Japan, was found to produce new biologically active substances. These substances, which are antibiotics, were extracted from the culture broth using n-butanol and purified by column chromatographies followed by preparative HPLC. Three preferred compounds were identified as isodecyl-, isoundecyl- and isolauryl 5-hydroxyanthranilate, respectively, by spectral analyses.

Thus, the fermentation of Streptomyces sp. AA2802 or a mutant thereof and suitable isolation techniques may be used to produce the compounds of the invention.

A biologically pure culture of Streptomyces sp. strain No. AA2807, from which the compounds of the invention are derived, has been deposited with the America Type Culture Collection (ATCC) in Rockville, MD and has been added to its permanent collection under Accession Code ATCC 55289.

The ATCC deposit was made before the filing of this application and meets all the requirements of 35 USC 112 and the Budapest Treaty regarding such deposits.

DRAWINGS

DESCRIPTION OF THE INVENTION

Figure 1:
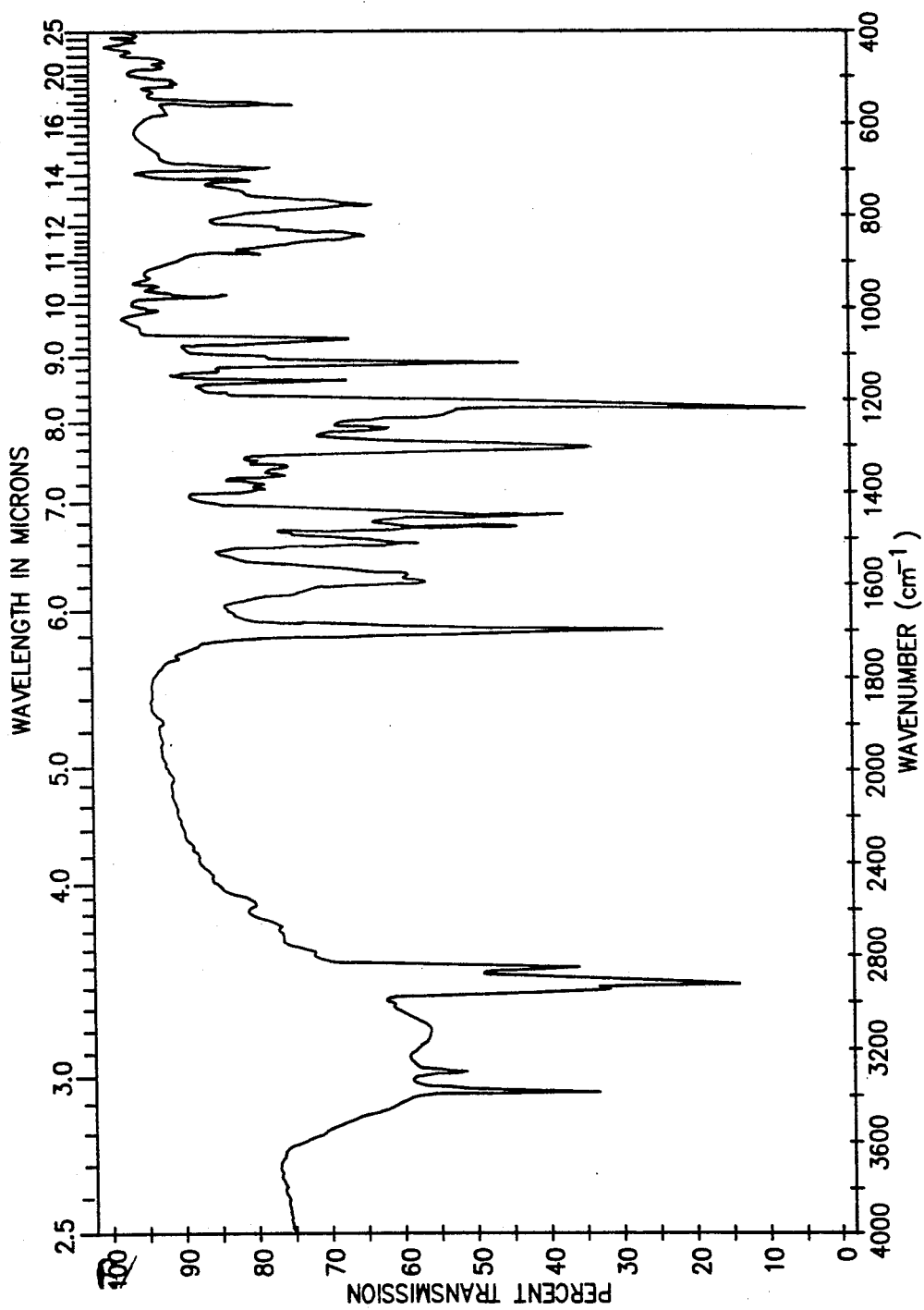
FIG. 1 shows the IR spectrum of Compound IC, isolauryl 5-hydroxyanthranilate (KBr).

A mixture of novel substances was isolated from a fermentation both of Streptomyces sp. AA2807 which detached from a submerged rotting leaf of seed in a marsh in Nagatoro, Saitama Prefecture, Japan. That mixture contained three compounds, all of which conform to structure I:

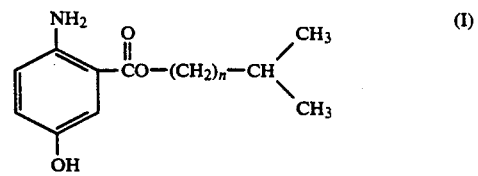

wherein n=7, 8 or 9.

These three compounds, designated IA n=7), IB (n=8) and IC (n=9) are, respectively, the isodecyl, isoundecyl and isolauryl esters of 5-hydroxyanthranilic acid.

Acid or base addition products, e.g., salts, of these compounds are also useful. Among the preferred addition products are those containing the ions hydrochloride, hydrobromide, sulfate, sodium, potassium, calcium and the like.

TAXONOMY

Morphology

The substrate mycelium was well-branched and non-fragmentary. Spore chains were formed on the monopodially branched aerial mycelium, which were long, straight or flexuous (Rectiflexibiles). These spores were oblong (0.6×1.0−1.2 μm) with smooth surface. Vegetative mycelium in submerged cultivation was partially septated, but not fragmented, and frequently single or longitudinal pairs of spore-likes were formed in the septated hypha.

Sclerotia, sporangia and zoospores were not observed.

Cultural and physiological characteristics

Growth and aerial mycelium formation were excellent on ISP-2 medium, and poor on ISP-3, 4, 5 and 7 media. The mass color of well sporulating aerial mycelium was gray (Gray color-series), but when the sporulation was poor, the color was brownish pink or yellowish gray.

Melanoid pigment was produced in ISP-1 and 6 media but not in ISP-7 medium. Growth occurred between 15° C. and 41° C. (optimal growth: 32° C.−37° C.), and in NaCl at 8% or less.

Tables 1 and 2, respectively, show cultural and physiological characteristics of the strain AA 2807.

Cell chemistry

Whole cell, phospholipid and menaquinone compositions were determined by the methods of Lechevalier[1]), Lechavalier et. al.[2]) and Minnikin et. al.[3]), respectively. Composition of methylesterified cellular fatty acids was analyzed by gas chromatography with SPB-I fused silica capillary column ($\phi$ 0.25 mm×30m), and by gas chromatographic mass spectrometry.

The whole cell hydrolysate contained LL-diaminopimelic acid and no characteristic sugar. Phospholipids contained phosphatidylethanolamine, phosphatidylinositol and phosphatidylinositol mannoside. Hence, strain AA2807 belongs to cell-wall type I and phospholipid pattern P-II. As shown in Tables 3 and 4, the major menaquinone was MK-9($H_8$) and MK-9($H_6$), and the fatty acid composition was pattern 2c[4]), since iso- and anteiso-branched fatty acids were the major components.

Notes:

(1) H Lechavalier, M. P. and H. Lechavalier, "Chemical methods as criteria for the separation of nocarciae and other actinomycetes", *Biology of the Actinomycetes and related Organisms*, 11, 1976, 78-92.

(2) Lechavalier, M. P.; C. D. Bievre and H. Lechavalier, "Chemotaxonomy of aerobic actinomycetes: Phospholipid compositions", *Biochem. Syst. Ecol*, 5, 1977, 249-260

(3) Minnikin, D. E.; L. Ashamanony and M Goodfellow, "Differentiation of Mycobacterium, Nocardia, and related taxa by thin-layer chromatographic analysis of

TABLE 1

Cultural characteristics of strain AA2807

| Medium | Growth | Aerial mycelium | Substrate mycelium | Diffusible pigment |
|---|---|---|---|---|
| Sucrose-nitrate agar | Scant | Absent | Colorless | None |
| Tryptone-yeast extract broth (ISP No. 1) | Moderate; pellicle, sediment and no turbidity | Poorly on pellicle; white | Colorless | Moderate brown (58) |
| Yeast extract-malt extract agar (ISP No. 2) | Good | Abundant; medium gray (265) | Deep brown (56) | Light yellowish brown (76) |
| Oatmeal agar (ISP No. 3) | Poor | Moderate; light gray (264) | Moderate yellowish brown (77) | Light Yellowish brown (76) |
| Inorganic salts-starch agar (ISP No. 4) | Moderate | Moderate; light gray (264) | Grayish reddish brown (46) | None |
| Glycerol-asparagine agar (ISP No. 5) | Moderate | Moderate; brownish pink (33) to light gray (264) | Grayish reddish brown (46) | None |
| Peptone-yeast extract-iron agar (ISP No. 6) | Good | Absent | Colorless | Black |
| Tyrosine agar (ISP No. 7) | Poor | Moderate; white to brownish pink (33) | Dark brown (59) | None |
| Glucose-asparagine agar | Good | Moderate; yellowish gray (93) | Grayish yellow (90) | Pale yellow (89) |
| Bennett's agar | Moderate | Absent or trace | Dark yellow (88) | Pale yellow (89) |
| Nutrient agar | Poor | Absent | Colorless | Dark brown (59) |

Observation after incubation at 28° C. for 2 weeks
Color names, used: ISCC-NBS Color-Name Charts

TABLE 2

Physiological characteristics of strain AA2807

| Hydrolysis of: | | D-Glucose | + |
|---|---|---|---|
| Gelatin | + | D-Galactose | + |
| Starch | + | D-Fructose | + |
| Casein | + | D-Mannose | + |
| | | L-Sorbose | − |
| Production of: | | Sucrose | + |
| Nitrate reductase | + | Lactose | − |
| Tyrosinase | + | Cellobiose | + |
| | | Melibiose | − |
| Tolerance to: | | Trehalose | + |
| Lysozyme, 0.001% | − | Raffinose | − |
| NaCl, 0~8% (w/v) | + | D-Melezitose | − |
| 10% (w/v) | − | Soluble starch | + |
| | | Cellulose | − |
| Temperature: | | Dulcitol | − |
| Growth range | 15° C.~41° C. | Inositol | + |
| Optimal growth | 32° C.~37° C. | D-Mannitol | + |
| No growth | 10° C. and 43° C. | D-Sorbitol | − |
| | | Salicin | + |
| Utilization of: | | | |
| Glycerol | + | Antibiosis against: | |
| D-Arabinose | − | *Bacillus subtilis* | − |
| L-Arabinose | + | (ATCC6633) | |
| D-Xylose | + | *Candida albicans* | − |
| D-Ribose | − | (A9540) | |
| L-Rhamnose | + | | |

*Basal medium: Pridham-Gottlieb's inorganic medium, ISP No. 9 whole-organism methanolysates", *J. Gen. Microbiol.*, 88, 1875, 200–204.

(4) Kroppenstedt, R. M.: "Fatty acid and menaquinone analysis of actinomycetes and related organisms", *Chemical Methods in Bacterial Systematics, The Society for Applied Bacteriology Technical Series No. 20*, (1985), 173–199.

TABLE 3

Menaquinone composition of strain AA2807
Menaquinone composition (%)

| MK-8 | | | MK-9 | | | | |
|---|---|---|---|---|---|---|---|
| $H_4$ | $H_6$ | $H_8$ | $H_2$ | $H_4$ | $H_6$ | $H_8$ | $H_{10}$ |
| 1 | 4 | 6 | 2 | 8 | 31 | 44 | 4 |

TABLE 4

Fatty acid composition of strain AA2807
Fatty acid composition (%)*

| Straight chain | | | | Branched chain | | | | | Unsaturated | | 10-Methyl i- fatty acids | Hydroxylated fatty acids |
|---|---|---|---|---|---|---|---|---|---|---|---|---|
| | | | | | | | | | i-16:1 | Cis9 16:1 | i-17:1 | |
| 15:0 | 16:0 | 17:0 | 18:0 | i-14 | i-15 | i-16 | a-15 | a-17 | | | | |
| 2 | 9 | 2 | | 22 | 10 | 21 | 11 | 14 | 2 | 9 | 6 | 0 | 0 |

*A blank number (%) means less than 1%

Taxonomic position

Although strain AA2807 was isolated from a rotting leaf of reed in aquatic environments, the morphological, cultural and physiological characteristics, and cell chemistry indicated that the strain belongs to the genus Streptomyces. According to the descriptions of Waksman[5]), Pridham and Tresner[6]), Shirling and Gottlieb[7,8]), and Williams et. al.[9]), strain AA2807 is related to *Streptomyces Achromogenes* Okami & Umezawa 1953, *Streptomyces diastaticus* (Krainsky 1914) Waksman & Henrici 1948, *Streptomyces nigrifaciens* Waksman 1961, and *Streptomyces fulvissimus* (Jensen 1930) Waksman & Henrici 1948 (See Table 5, infra).

Notes:

(5) Waksman, S. A., "Classification, identification and descriptions of genera and species", (6) *The Actinomycetes*. Vol. 2. (1961) pp. 165–292. Pridham, T. G. and H. D. Tresner, "Genus Streptomyces Waksman and Henrici 1943", *Bergey's Manual of Determinative Bacteriology*, 8th ed (1974) pp. 748–829.

(7) Shirling, E. G. and D. Gottlieb, "Cooperative description of type cultures of Streptomyces II: Species descriptions from first study", *Int. J. Syst. Bacteriol.*, 18 (1968) pp. 69–189.

(8) Shirling, E. B. and D. Gottlieb, "Cooperative description of type strains of Streptomyces, V. Additional descriptions.," *Int. J. Syst. Bacteriol.*, 22, (1972) pp. 265–394.

(9) Williams, S. T.; M. Goodfellow and G. Alderson, "Genus Streptomyces Waksman and Henrici 1943.", *Bergey's Manual of Systematic Bacteriology*, Vol. 4 (1989) pp. 2452–2492.

However, the taxonomic relationships between the strain and these four species are not considered to be well established. Therefore, strain AA2807 was identified as Streptomyces sp.

TABLE 5

Comparisons between strain AA2807 and four related species of Streptomyces

| | Strain AA2807 | S. achromogenes | S. diastaticus | S. nigrifaciens | S. fulvissimus |
|---|---|---|---|---|---|
| Spore chain | RF | RF | RF/S | RF | RF |
| Spore surface | SM | SM | SM | SM | SM |
| Spore mass color | Gray | Gray | Gray yellow | Gray | Yellow red |
| Growth on sucrose-nitrate agar | Scant | Poor | Poor | Poor | Good |
| Melanin | + | + | + or − | − | + |
| Other pigments | − | − | − | +(black) | +(red) |
| Nitrate reduction | + | + | + | + | + |
| NaCl tolerance (%) | ≧7, <10 | ≧7, <10 | | ≧7, <10 | ≧7, <10 |
| Utilization of: | | | | | |
| D-Xylose | + | − | + | + | v |
| L-Rhamnose | + | v | − | + | − |
| Sucrose | + | − | + | − | − |
| Raffinose | − | − | − | − | + |
| Inositol | + | v | − | − | + |

Abbreviations
Spore chain: RF, Rectiflexibiles; S, Spirales.
Spore surface: SM, smooth.
+, positive; −, negative; v, variable.

Fermentation

Stocked culture

Strain AA2807 was propagated on Bn-3 agar slant composed of soluble starch (Nippon Starch Chemical Co.) 0.5%, glucose 0.5%, meat extract (Mikuni Kagaku Kougyo Co.) 0.1%, yeast extract (Oriental Yeast Co.) 0.1%, NZ-case (Humko Sheffield Chemical Co.) 0.2%, NaCl 0.2%, $CaCO_3$ 0.1% and agar (Junsei Chemical Co.) 1.6%. After incubation for 14 days at 28° C., a portion of the mature agar slant was inoculated into 100 ml of a seed medium in a 500-ml Erlenmeyer flask and incubated at 28° for 4 days on a rotary shaker at 200 rpm. The seed medium was consisted of soluble starch 2.0%, glucose 0.5%, NZ-case 0.3%, yeast extract (Nihon Seiyaku) 0.2%, fish meal D30X (Banyu Nutrient Co.) 0.5% and calcium carbonate 0.3%.

The resulting vegetative mycelia were spun down gently (3,000 rpm, 15 minute, 4° C.). Harvested mycelia were resuspended in a half volume of 20% glycerol solution and then stocked at −80° C.

Seed culture

A stocked frozen culture of the producing strain was inoculated into 100 ml of a seed medium in a 500-ml Erlenmeyer flask and incubated at 28° C. for 4 days on a rotary shaker at 200 rpm.

Flask fermentation

A 5-ml of the seed culture was transferred into 500-ml Erlenmeyer flasks each containing 100 ml of a production medium and incubated for 112 hours under the same conditions as those for the seed culture. The production medium was consisted of soluble starch 3.0%, beet molasses (Nihon Tensai Seito) 0.5%, Protein-S (Ajinomoto Co., Inc.) 2.0%, fish meal (Hokuyo Suisan) 0.5% and calcium carbonate 0.3%. The pH of the medium was adjusted to 7.0 before autoclaving.

Isolation and purification

The harvested broth (9 liters) was stirred with n-butanol (5 liters) for two hours. The organic extract (4.5 liters) was separated from the broth using a Sharpless type centrifuge (Kokusan No. 4A) and concentrated in vacuo to afford a crude solid (5.6 g). This solid was partitioned between ethyl acetate and water (200 ml each). The ethyl acetate layer was concentrated in vacuo and the residue applied onto a silica gel column (Wako gel C-200, 4.0 i.d. ×56 cm) which had been pretreated with methylene chloride. The column was developed by methylene chloride with an increasing amount of methanol (2–10%, v/v). The eluate was collected in 15 ml fractions which were monitored by 5-lipoxygenase inhibitory activity and TLC ($SiO_2$, methylene chloride-methanol 20:1, v/v). The appropriate fractions were collected, and concentrated in vacuo. The concentrate was rechromatographed on a column of silica gel (Wako gel C-300, 3.0 i.d. ×60 cm) using methylene chloride-methanol (10:1 v/v) as a developing solvent to afford a purified solid (114 mg) of a mixture of compounds IA, IB and IC. The mixture (96 mg) was further purified by preparative HPLC using a YMC-ODS, D-ODS-5 column (20 i.d. ×250 mm, Yamamura Chemical Lab.) and 75~90% aqueous acetonitrile (linear gradient) as a eluent. Upon monitoring by HPLC, the appropriate fractions were combined and concentrated in vacuo to yield IA (2.5 mg), IB (2.4 mg) and IC (9.3 mg) as amorphous pure powder.

Physico-chemical properties

Compounds IA, IB and IC are amorphous white powders. They are soluble in methanol, ethanol, ethyl acetate, chloroform and dimethyl sulfoxide, slightly soluble in n-hexane, but insoluble in water. They gave positive response to iodine vapor, sulfuric acid and ferric chloride, but negative to ninhydrin and anthrone tests. The EI-MS spectra of the compounds showed the molecular ions at m/z 293, 307 and 321, respectively.

Figure 2:
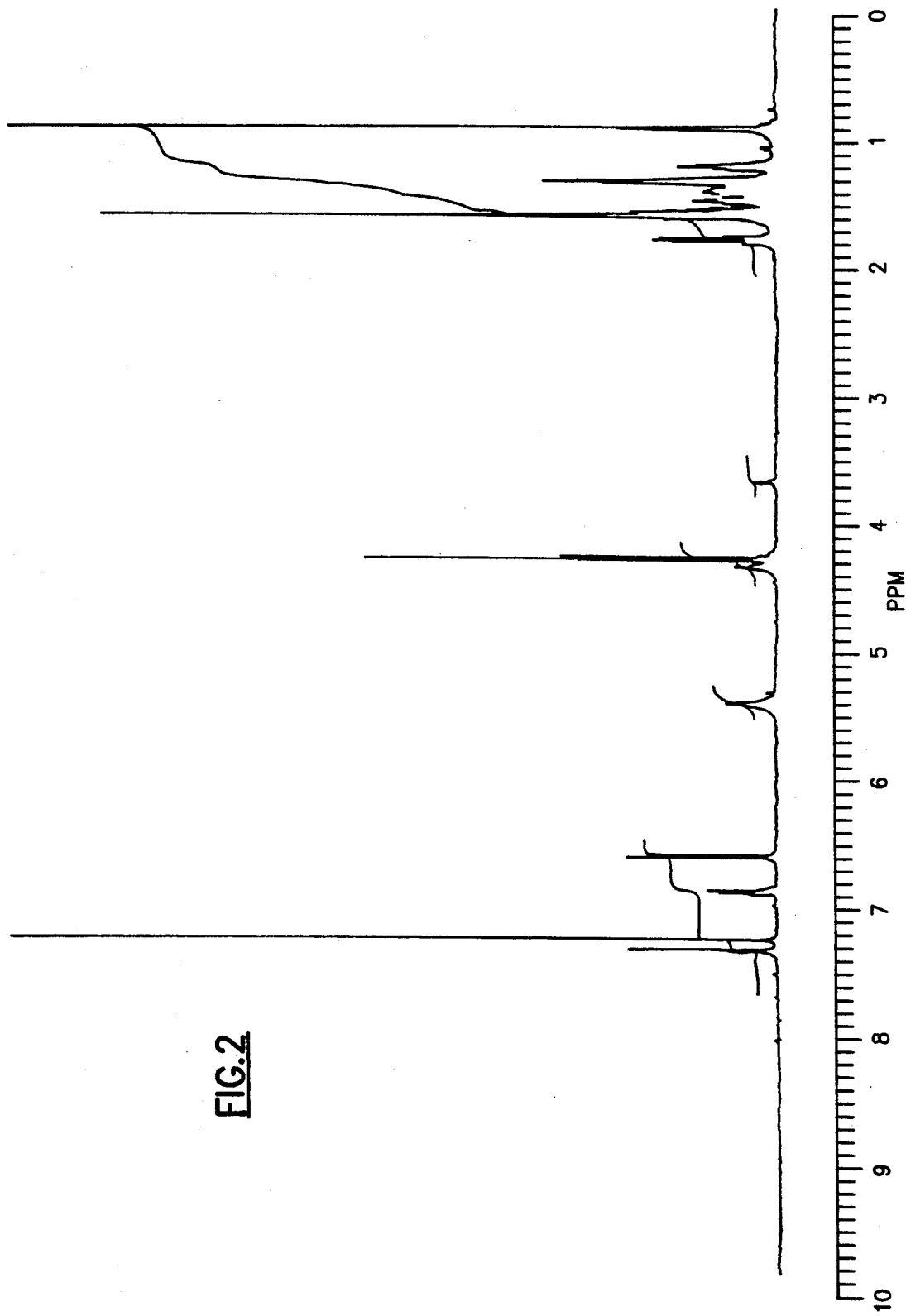
FIG. 2 is the $^1$H-NMR spectrum compound IA, isodecyl 5-hydroxyanthranilate (400 MHZ, $CDCl_3$)
Figure 3:
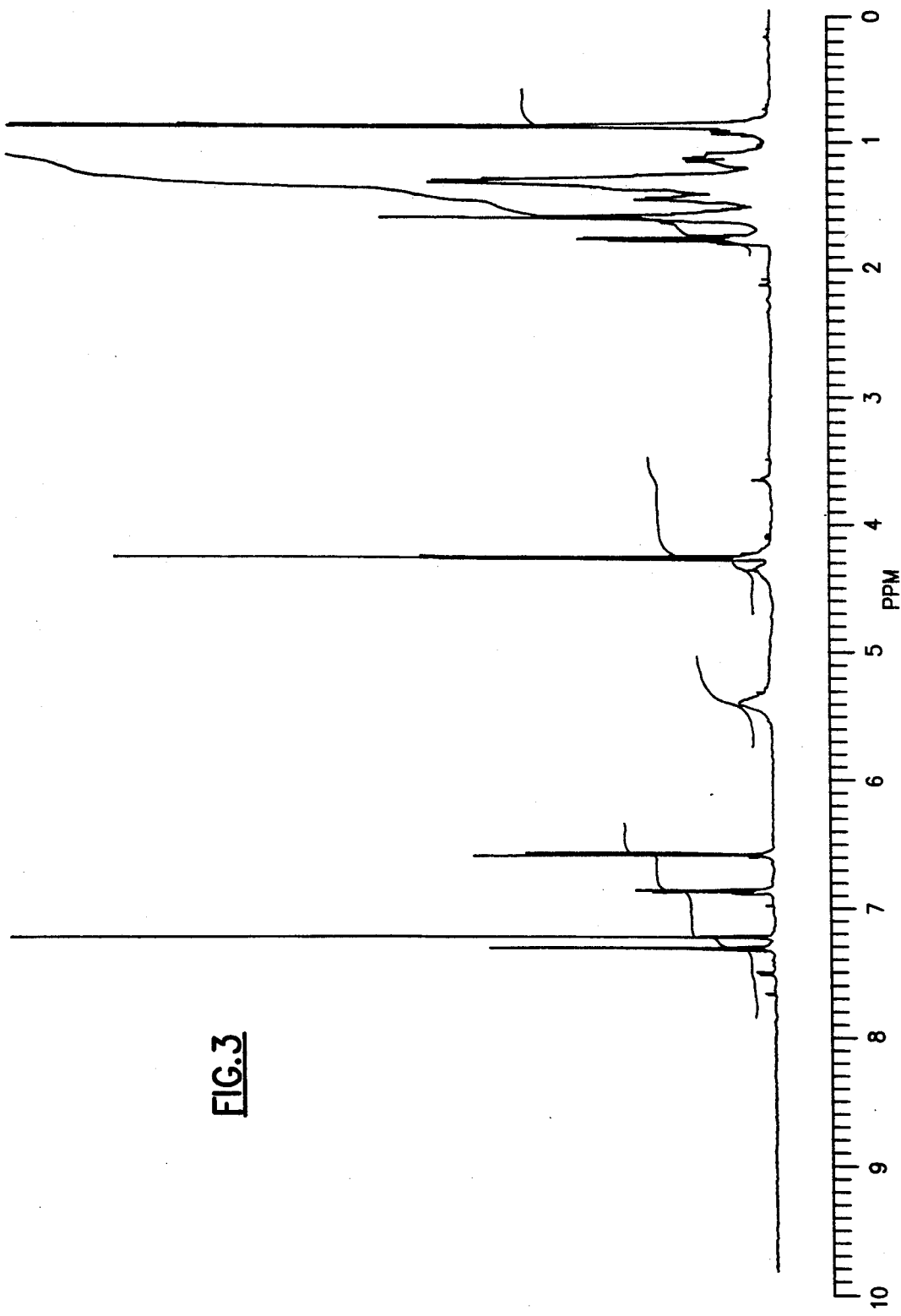
FIG. 3 is the $^1$H-NMR spectrum of compound IB, isoundecyl 5-hydroxyanthranilate (400 MHz, $CDCl_3$)
Figure 4:
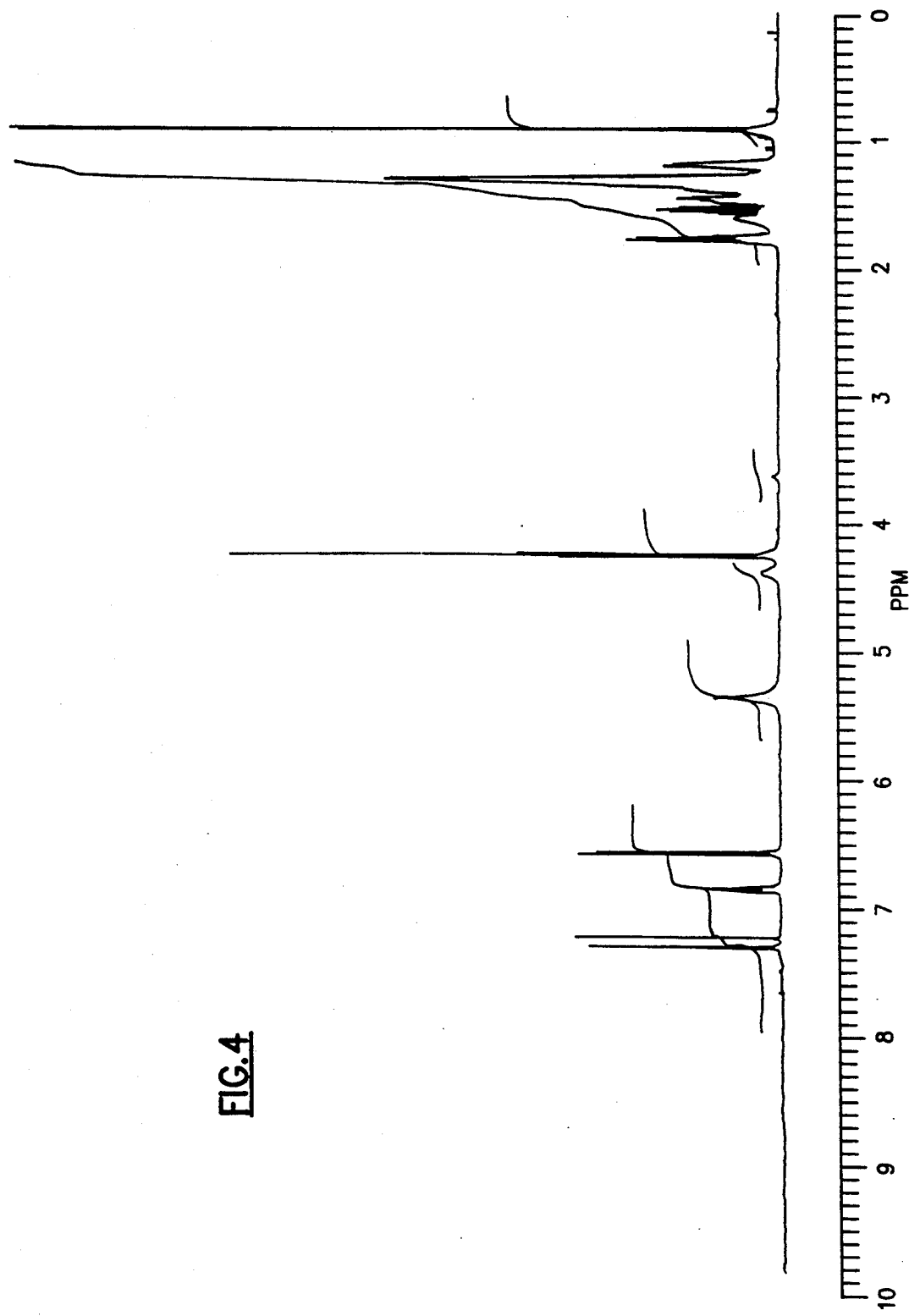
FIG. 4 is the $^1$H-NMR spectrum of compound IC, isolauryl 5-hydroxyanthranilate (400 MHz, $CDCl_3$).
Figure 5:
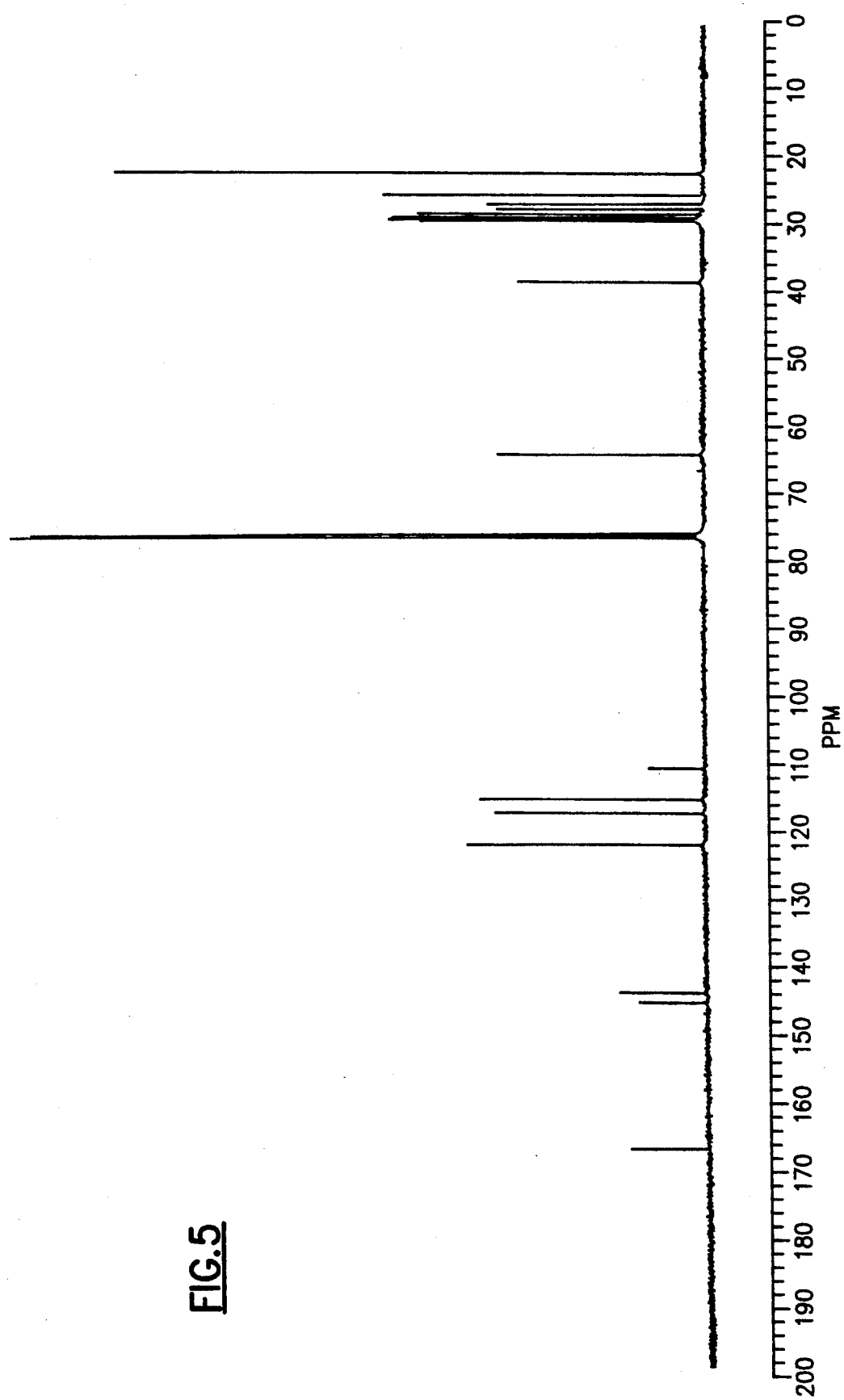
FIG. 5 is the 13C-NMR spectrum of compound IC, isolauryl 5-hydroxyanthranilate (100 MHz, $CDCl_3$)

The molecular formulae of IA, IB and IC were established as $C_{17}H_{27}NO_3$, $C_{18}H_{29}NO_3$ and $C_{19}H_{31}NO_3$, respectively, based on the mass spectra and $^1H$ and $^{13}C$-NMR spectra (Tables 7 and 8). Their physico-chemical data are summarized in Table 6. The UV spectra of these substances are very similar to each other, exhibiting absorption maxima at 220, 245(sh) and 359 nm in methanol, 211, 234, 301 and 351 nm in 0.01N NaOH-MeOH and 224, 260(sh) and 370 nm in 0.01N NaOH-MeOH. The IR spectrum (FIG. 6) of IC showed absorption bands at 3395, 3305, 2930, 2855, 1700, 1595, 1510, 1475, 1445, 1305, 1210, 1120 and 1070 $cm^{-1}$. The $^1H$-NMR spectral data (FIGS. 2, 3 and 4. Table 7) of these components exhibit two methyl ($\delta 0.86$, 6H, d), one low field methylene ($\delta 4.25$, d) one methene ($\delta 1.58$, m), three aromatic protons ($\delta 6.59$, 6.88 and 7.34), one amino ($\delta 5.38$) and one phenolic hydroxyl group ($\delta 4.39$) together with high field methylene protons ($\delta 1.1 \sim 1.7$) corresponding to six, seven and eight methylene groups of IA, IB and IC, respectively. The $^{13}C$-NMR spectral data (Table 8 and FIG. 5) of IC showed 19 carbon signals including two methyl, nine methylene, one methine and six $sp^2$ carbons together with one carbonyl carbon ($\delta 167.8$).

Structure determination

The similar UV absorptions of the three substances indicated a common chromophore. The IR spectrum (FIG. 1) of IC showed the presence of amino (3395 $cm^{-1}$), hydroxyl (3150 $cm^{-1}$), ester (1700, 1210 & 1120 $cm^{-1}$) and aromatic (1595 & 1570 $cm^{-1}$) functionalities. The EI-MS spectra of IA, IB and IC showed a molecular ion at m/z 293, 307 and 321, respectively, together with common fragment ions at m/z 153 ($C_7H_7NO_3$) and 135 ($C_7H_5NO_2$) which were deduced to be a benzoic acid substituted with one amino and one hydroxyl group. The $^1H$-NMR spectra (FIGS. 2, 3 and 4; Table 7) of the three components are very similar containing three aromatic protons ($\delta 6.59$, 6.88 & 7.34) and isopropyl protons ($\delta 0.84$, 6H, d and 1.58 1H, m), but they differed from each other in the number of methylene groups. These EI-MS and $^1H$-NMR data clearly indicated that IA, IB and IC were different in only the number of methylene groups ($CH_2 \times 7$, $CH_2 \times 8$ and $CH_2 \times 9$, respectively ) in their alkyl side chains. The aromatic protons ($\delta 6.59$, 6.88 and 7.34) were assignable to the 1, 2, 4-trisubstituted benzene ring on the basis of their coupling constants (J: 3.0 & 8.9 Hz). The spectrum also indicated one amino ($\delta 5.40$) and one hydroxyl group ($\delta 4.34$). This information, together with the UV and EI-MS data suggested 5-hydroxyanthranilate structures for IA, IB and IC[10-15]. This was confirmed by comparison of their spectral data with those of methyl 5-hydroxyanthranilate[10] which was prepared from 5-hydroxyanthranilic acid by diaxomethane methylation. The $^1H$-NMR data and the fragment ion (m/z 153, $M^+$-$C_{12}H_{25}$) observed in the EI-MS spectrum of IC indicated an isolauryl ester in the molecule. The carbon signals in $^{13}C$-NMR spectrum (FIG. 5 and Table 8) of IC were analyzed as two methyl $22.6 \times 2$), nine methylene groups ($\delta 26.1$, 27.3, 28.7, 29.3, 29.5, 29.6, 29.9, 39.0 and 64.7) and one methene carbon ($\delta 27.9$) by DEPT experiment supporting the presence of an isolauryl ester unit. The spectrum exhibited six aromatic carbons ($\delta 111.6$, 116.1, 118.2, 122.9, 144.9 and 146.1) and an ester carbon ($\delta 167.8$) due to a 5-hydroxyanthranilate moiety. As discussed before, the EI-MS and $^1H$-NMR data exhibited that the three compounds differed in only the number of methylene linkages in the alkyl side chains. IA and IB were shown to have $CH_2 \times 2$ and $CH_2$, respectively, shorter alkyl side chains than that of IC by the spectral data. Thus, the structures of IA, IB and IC were determined as isodecyl, isoundecyl and isolauryl 5-hydroxyanthranilate, respectively.

NOTES:

(10) van der Stelt, C.; B. G. Suurmond & W. Th. Naute, "The Hofmann degradation of 4-hydroxyphthalimide", *Recueil.* 72, (1953), pp. 195–201.

(10) Rodionow, W. M. & A. M. Fedorowa, "Memoires presentes a la societe chimique. Contribution a l'etude de l'acide anthranilique mono-et dimethoxyle et de leus derives", *Bull. Soc. Chim. Fr.*, 5(6), (1939), pp. 478–486.

(12) Mazaki, M.; Y. Nomura, T. Yamakawa & H. Takeda (Nippon Chemiphar), "Processes for production of anthranilate", *Jpn. Kokai* 287755 ('88), Nov. 24, 1988.

(13) Mazaki, M.: Y. Nomura, T. Yamakawa & H. Takeda (Nippon Chemiphar), "5-Alkoxyanthranilate", *Jpn. Kokai* 290856 ('88), Nov. 28, 1988.

(14) Mazaki, M.; Y. Nomura, T. Yamakawa & H. Takeda (Nippon Chemiphar), "Processes for production of 5-hydroxyanthranilate", *Jpn. Kokai* 303959 ('88) Dec. 12, 1988.

TABLE 6
Physico-chemical properties of Compounds IA, IB and IC.

| | IA | IB | IC |
|---|---|---|---|
| Nature: | White amorphous powder | White amorphous powder | White amorphous powder |
| $[\alpha]_D^{27}$ | −10 ± 2.0° (C 0.1, MeOH) | −28 ± 4.0° (C 0.05, MeOH) | −28 ± 6.0° (c 0.05, MeOH) |
| UV $\lambda_{max}$nm ($\epsilon$) in MeOH: | 220(28.200) 246(sh) 359(5,800) | 219(24,600) 246(sh) 360(5,200) | 219(23,300) 246(sh) 360(4,800) |
| in 0.01N HCl: —MeOH | 211(30,900) 233(sh) 300(4,400) | 212(29,200) 234(9,100) 300(3,800) | 212(26,000) 234(8,000) 300(3,600) |
| in 0.01N NaOH: —MeOH | 208(34,700) 225(24,200) 372(4,500) | 208(33,800) 225(24,600) 372(4,600) | 208(33,900) 223(21,700) 372(4,100) |
| IR(KBr) cm$^{-1}$: | | | 3395,3305,2930,1700, 1595,1510,1445,1305, 1210,1120,840,785 |
| Molecular formula: | $C_{17}H_{27}NO_3$ | $C_{18}H_{29}NO_3$ | $C_{19}H_{31}NO_3$ |
| EI-MS m/z: | 293(M$^+$) | 307(M$^+$) | 321(M$^+$) |
| HPLC (Rt): | 4.9 min | 6.5 min | 9.4 min |

(Column: A-301-3-S-3 120A ODS, 4.5 i.d. × 100 mm, YMC)
(Mobile phase: CH$_3$CN—H$_2$O = 3:1 v/v)

TABLE 7
$^1$H—NMR spectra of IA, IB and IC (400 MHz in CDCl$_3$)

| Proton | IA | IB | IC |
|---|---|---|---|
| 1&2-CH$_3$ | 0.86(6H, d, J=6.5Hz) | 0.86(6H, d, J=6.8Hz) | 0.86(6H, d, J=6.8Hz) |
| 3-CH | 1.53(1H, m) | 1.58(1H, m) | 1.58(1H, m) |
| 4-CH$_2$ | 1.17(2H, m) | 1.13(2H, m) | 1.15(2H, m) |
| —(CH$_2$)$_n$— | 1.26 / 1.37 (6H, m) | 1.25 / 1.35 (8H, m) | 1.2 / 1.4 (10H, m) |
| 5-CH$_2$ | 1.43(2H, m) | 1.43(2H, m) | 1.42(2H, m) |
| 3'-H | 6.60(1H, d, J=8.9Hz) | 6.60(1H, d, J=8.5Hz) | 6.59(1H, d, J=8.5Hz) |
| 4'-H | 6.88(1H, dd, J=8.9&3.0Hz) | 6.88(1H, dd, J=8.5&3.0Hz) | 6.88(1H, dd, J=8.5&3.0Hz) |
| 6'-H | 7.34(1H, d, J=3.0Hz) | 7.34(1H, d, J=3.0Hz) | 7.34(1H, d, J=3.0Hz) |
| 2'-NH$_2$ | 5.38(2H, br, NH$_2$) | 5.40(2H, br, NH$_2$) | 5.38(2H, brs, NH$_2$) |
| 5'-OH | 4.31(1H, brs, OH) | 4.34(1H, br, OH) | 4.39(1H, br, OH) |

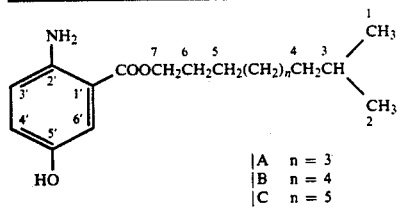

|A  n = 3
|B  n = 4
|C  n = 5

TABLE 8
$^{13}$C—NMR spectrum of IC (100 MHz in CDCl$_3$)

| C-1 & 2 | 22.6(q) × 2 | C-12 | 64.7(t) |
|---|---|---|---|
| C-3 | 27.9(d) | C-13 | 167.8(s) |
| C-4~C-10 | 26.1(t) 27.3(t) 28.7(t) 29.3(t) 29.5(t) 29.6(t) 29.9(t) | C-1' C-2' C-3' C-4' C-5' C-6' | 111.6(s)* 146.1(s)** 116.1(d)** 122.9(d)** 144.9(s)* 118.2(d)** |

TABLE 8-continued
$^{13}$C—NMR spectrum of IC (100 MHz in CDCl$_3$)

| C-11 | 39.0(t) |
|---|---|

*,**: The chemical shifts may be interchanged.

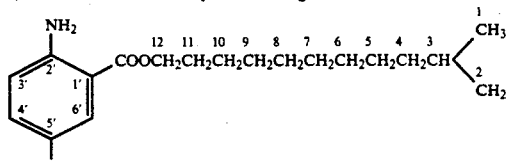

IC

Compositions and Methods

The novel compounds of the invention can be used in a variety of pharmaceutical dosage forms. Thus oral, parenteral, nasal, topical, buccal, ocular and other forms can be used. When such forms are formulated, they will include pharmaceutically acceptable excipients such as colorants, carriers, perfumes, stabilizers, flow modifiers and the like in suitable amounts (i.e., from 0.001 to 0.99 wt%).

The compounds of the invention are useful in methods of inhibiting the effects of 5-LPO.

The compound of formula I may also be used to treat a host, preferable a mammal, which is suffering from a disorder associated with the metabolism of 5-LPO, such as asthma, hypersensitivity, psoriasis and other inflammatory conditions.

EXAMPLE

The following example illustrates the 5-lipoxygene inhibitor effects of the novel compounds.

Experimental

The assay method employed in this manuscript is a slight modification of that published by Hook, Yacobuci, O'Connor, Lee, Kerns, Krishnan, Matson and Hesler in "Identification of the inhibitory activity of carbazomycins B and C against 5-lipoxygenase: a new activity for these compounds", *J. Antibiot.* (1990) 43, 1347. Rat basophilic leukemia cells heat-inactivated fetal bovine serum (GIBCO). They were harvested by centrifugation and washed twice with 28.5 mM pH 7.0 containing I mM EDTA. The cells were resuspended in the same buffer and sonicated. The suspension was centrifuged at 13,000×g to remove cell debris and the supernatant stored at −80° C.

Enzyme assays were conducted by diluting the cell-free extract to the desired specific enzyme activity with phosphate buffer saline (PBS) containing 28.5 mM phosphate, 1 mM ethylenediamine tetraacetic acid (EDTA), 0.9 mM adenosine triphosphate (ATP) and 0.9 mM glutathione. The cell-free extract solution (110 μl) was preincubated at 37° C. for 2.5 minutes, followed by the addition of the test sample in 20 μl of DMSO-PBS (1:9, v/v). The reaction was started by the addition of 5 μl of substrate (2 mM arachidonic acid plus 25 mM CaCl2 in ethanol-water, 3:1). After incubation for 5 minutes, the reaction was terminated by the addition of 135 μl of ethanol and the solution centrifuged to remove precipitated protein. The 5-hydroxyeicosatetraenoic acid (5-HETE) in the supernatant was analyzed by HPLC as described below.

5-HETE Analysis

The inhibitory effect of a fermentation broth extract or a purified preparation was determined by measuring the amount of 5-hydroxyeicosatetraenoic acid (5-HETE) produced in a cell-free extract of rat basophilic leukemia cells (RBL-I cells, ATCC CRL 1378) in the presence of a test sample, arachidonic acid, adenosine triphosphate, CaCl2 and glutathione. The 5-HETE produced was separated by high performance liquid chromatography (HPLC, Rainin Dynamax C18, 5cm×0.46cm) with an HpLC solvent Of 82% MeOH-18% 29.2 mM lithium acetate buffer, pH 6.3 at a flow rate of 1 ml/minute. The concentration of 5-HETE was spectrophotometrically measured at 230 nm with a Gilson 115 UV detector and a Hewlett Packard 3396 A integrator.

Results

The compound (I) was discovered in the fermentation broth of a species of Streptomyces No. AA2807. Three components, IA, IB and IC, were successfully purified to homogeneity. The $IS_{50}$ values of three components for rat 5-LPO inhibitory activity were determined and described in Table 9.

TABLE 9

| 5-LPO Inhibitory Activity of the Novel Compounds IA, IB and IC | |
|---|---|
| Compound | $IC_{50}$ (in μ moler) |
| IA Isodecyl 5-hydroxyanthranilate | 3.4 |
| IB Isoundecyl 5-hydroxyanthranilate | 4.9 |
| IC Isolauryl 5-hydroxyanthranilate | 6.3 |

Reasonable variations, such as those which would occur to a skilled artisan, can be made herein without departing from the scope of the invention.

We claim:

1. A novel compound of structure I:

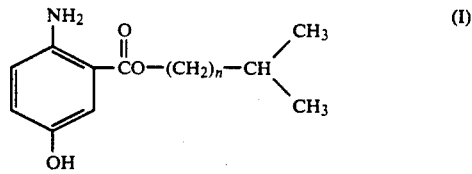

wherein n=7, 8 or 9, or a pharmaceutically acceptable derivative thereof.

2. An acid or base addition product of the compound of claim

3. The compound of claim 1 wherein n=7.

4. The compound of claim I wherein n=8.

5. The compound of claim 1 wherein n=9.

6. A pharmaceutical preparation containing an effective amount of the compound of claim 1 and one or more pharmaceutically acceptable excipients.

* * * * *